(12) United States Patent
Snyder et al.

(10) Patent No.: US 8,197,123 B2
(45) Date of Patent: Jun. 12, 2012

(54) THERMISTOR CIRCUIT CALIBRATION

(75) Inventors: Robert L. Snyder, Suwanee, GA (US); Maurice Wheatley, Duluth, GA (US)

(73) Assignee: Smiths Medical ASD, Inc., Rockland, MA (US)

( * ) Notice: Subject to any disclaimer, the term of this patent is extended or adjusted under 35 U.S.C. 154(b) by 416 days.

(21) Appl. No.: 11/927,000

(22) Filed: Oct. 29, 2007

(65) Prior Publication Data

US 2009/0110022 A1    Apr. 30, 2009

(51) Int. Cl.
*G01K 7/16* (2006.01)
*G01K 7/22* (2006.01)
*G01K 7/25* (2006.01)
*G01K 15/00* (2006.01)

(52) U.S. Cl. ............ 374/1; 374/170; 374/185; 374/172; 374/173; 702/99; 702/130; 600/549

(58) Field of Classification Search ............... 374/1, 2, 374/100, 163, 170–173, 183, 185, 4–5, 164, 374/57, 141; 327/512, 513; 702/99, 130–136, 702/139; 324/601; 600/549, 474

See application file for complete search history.

(56) References Cited

U.S. PATENT DOCUMENTS

| | | | | |
|---|---|---|---|---|
| 4,312,358 A | * | 1/1982 | Barney | 600/483 |
| 4,473,797 A | * | 9/1984 | Shiota | 324/115 |
| 4,901,257 A | * | 2/1990 | Chang et al. | 702/99 |
| 4,958,139 A | * | 9/1990 | Hyatt | 341/139 |
| 4,994,653 A | * | 2/1991 | Kadwell et al. | 219/508 |
| 5,095,453 A | * | 3/1992 | Pierson et al. | 702/99 |
| 5,144,814 A | | 9/1992 | Gaudette | |
| 5,361,637 A | * | 11/1994 | Judd et al. | 73/766 |
| 5,669,713 A | | 9/1997 | Schwartz et al. | |
| 5,689,447 A | * | 11/1997 | Ward | 702/99 |
| 5,781,098 A | * | 7/1998 | Shibata | 338/28 |
| 5,943,473 A | | 8/1999 | Levine | |
| 6,054,887 A | * | 4/2000 | Horie et al. | 327/307 |
| 6,078,730 A | | 6/2000 | Huddart et al. | |
| 6,402,371 B2 | * | 6/2002 | Pompei et al. | 374/128 |
| 6,515,464 B1 | * | 2/2003 | Darmawaskita et al. | 324/76.11 |
| 6,577,480 B1 | * | 6/2003 | Avery et al. | 361/56 |
| 6,908,224 B2 | | 6/2005 | Schneider et al. | |
| 6,931,331 B2 | * | 8/2005 | McTigue | 702/57 |

(Continued)

FOREIGN PATENT DOCUMENTS

JP          09232956 A    *    9/1997

OTHER PUBLICATIONS

Manual for Fisher & Paykel Model Nos. MR700, MR720, MR730 Respiratory Humidifiers (Mar. 1998) (48 pages).
Technical Manual Fisher & Paykel Respiratory Humidifier Model Nos. MR700, MR720, MR730, MR 480 (Mar. 2001) (64 pages).
Allegiance Healthcare 510K No. K993833 for Airlife® Heated Ventilator and Anesthesia Breathing Circuits (5 pages) (Dec. 10, 1999).

(Continued)

*Primary Examiner* — Gail Verbitsky
(74) *Attorney, Agent, or Firm* — Kurt L. Grossman

(57) ABSTRACT

Temperature detection circuitry is selectively coupled to a thermistor and one of two sources representing the impedance at respective ends of the expected range of temperature to which the thermistor is to be exposed. The offset of an amplifier and a scale factor to account for gain set of the amplifier are determined in an automatic calibration process while coupled to the source(s), and thereafter temperature readings are taken from the thermistor. During the calibration process, if the gain or scale factor are outside of expected ranges, a failure is determined and an alarm given and/or a heater is disabled.

22 Claims, 3 Drawing Sheets

U.S. PATENT DOCUMENTS

| | | | |
|---|---|---|---|
| 6,988,497 B2 | 1/2006 | Levine | |
| 7,223,014 B2* | 5/2007 | Lojen | 374/120 |
| 2002/0079310 A1* | 6/2002 | Siefert | 219/494 |
| 2002/0150140 A1* | 10/2002 | Julicher et al. | 374/120 |
| 2003/0065467 A1* | 4/2003 | Schuh et al. | 702/99 |
| 2004/0102914 A1* | 5/2004 | More | 702/99 |
| 2004/0170213 A1* | 9/2004 | Rund et al. | 374/170 |
| 2006/0104330 A1* | 5/2006 | Ho Limb et al. | 374/1 |
| 2006/0119424 A1* | 6/2006 | Ha et al. | 330/9 |
| 2008/0027667 A1* | 1/2008 | Petersen et al. | 702/104 |
| 2008/0054497 A1 | 3/2008 | Bradley et al. | |
| 2008/0054500 A1 | 3/2008 | Bradley et al. | |
| 2009/0110023 A1* | 4/2009 | Clark et al. | 374/1 |
| 2009/0154519 A1* | 6/2009 | Price | 374/1 |
| 2009/0262776 A1* | 10/2009 | Limb et al. | 374/1 |
| 2009/0296769 A1* | 12/2009 | Fiennes et al. | 374/1 |
| 2009/0302923 A1* | 12/2009 | Smeloy et al. | 327/307 |

OTHER PUBLICATIONS

Brochure for Hudson RCI Humid-Heat® (6 pages).
Operating Manual for Fisher & Paykel Model Nos. MR700, MR720, MR730 Respiratory Humidifiers (Mar. 1994) (46 pages).
Instruction Sheet for Airlife® Single Heated Adult Respiratory Circuit (2 pages).
Cardinal Health RT110 Data for Circuits, reprinted from the internet Jun. 3, 2006 (2 pages).
Fisher & Paykel 900MR561 Temperature Probe Label (one page) (date uncertain).
Fisher & Paykel Airway Temperature Probes Instructions for Use (3 pages) (2003).
Cat. RT110 Insert for Airlife ™ Adult Respiratory Circuit—Heated (one page) (undated).

* cited by examiner

THERMISTOR CIRCUIT CALIBRATION

FIELD OF THE INVENTION

The present invention generally relates to circuitry adapted to obtain temperature readings from a thermistor, and more particularly to automatic calibration in relation to such circuitry in a respiratory system.

BACKGROUND OF THE INVENTION

Respiratory systems provide breathable gas, such as oxygen, anesthetic gas and/or air directly to a patient's mouth, nose or airway to assist or facilitate breathing by the patient. A ventilator may be used as part of the respiratory system to drive the breathable gas to the patient through an inspiratory limb hose or conduit of a breathing circuit. The breathing circuit may include an expiratory limb hose or conduit to carry expelled air and other gas(es) from the patient back to the ventilator.

It is typically desired to warm and impart humidity to the breathable gas before it is provided to the patient. For that purpose, many respiratory systems include a humidification system having a heater unit and a disposable water chamber adapted to be heated by the heater unit. The heater unit supports a hot plate heater, which may be comprised of one or more heating elements and a metal plate defining a hot plate. A wall of the chamber, such as the bottom surface of the chamber, is thermally conductive. The chamber is removably supported on the heater unit with the bottom surface in thermal contact with the hot plate of the heater unit to thus heat the water in the chamber. The chamber may be manually refillable, or there may be a water source to selectively fill the chamber as it empties. The breathable gas is coupled to the chamber and is passed through the chamber to be heated and humidified. The inspiratory limb carries the heated and humidified gas to the patient and the expiratory limb, if present, carries exhaled air and possibly other gases from the patient. Examples of heater units, chambers and vented water supplies are shown in U.S. Pat. Nos. 6,988,497 and 5,943,473; and co-pending U.S. patent application Ser. Nos. 11/469,086 and 11/469,113, both filed Aug. 31, 2006.

The hoses or conduits of the inspiratory and expiratory limbs may each be provided with a heater circuit to add heat to the gas passing through the limb. The heater circuit may be in the form of one or more elongated, and possibly coiled, heater wires running along the limb, such as through the interior of the limb. An example of a breathing circuit with heated limbs is shown in U.S. Pat. No. 6,078,730. The heater unit typically houses the necessary electrical and electronic components to regulate the temperature of the hot plate, as well as heating circuits of the inspiratory and/or expiratory limbs of the breathing circuit. To that end, the temperature of the gas passing through the breathing circuit may be monitored at various locations, two examples of which are at the outlet of the chamber (i.e., the inlet to the inspiratory limb) and/or at the outlet of the inspiratory limb (i.e., at the patient). The temperature of the hot plate may also be monitored. Those temperatures may each be monitored with a respective temperature responsive device that provides temperature readings as feedback to the heater unit for purposes of regulating the various heating components. The temperature responsive device may take the form of a thermistor coupled to the hot plate or held within a probe adapted to be inserted into the flow path of the gas through the limb.

Resistance of a thermistor varies in relation to the temperature to which the thermistor is exposed. Detection circuitry coupled to the thermistor can sense the resistance, such as by sensing a voltage induced across the thermistor by a constant current passing therethrough, and provide an output signal, such as in the form of a digital temperature signal or word, corresponding thereto (and thus to the temperature at the thermistor). The digital temperature signal may be utilized by a processor to generate a useful form of the digital temperature signal which should be correlated to the actual sensed temperature, such as by undertaking appropriate calculations or utilizing a look-up table(s), which produce the useful form of signal utilized by the processor or other circuitry of the heater unit to monitor and/or control the various heaters of the humidification system. The detection circuitry and processor thus cooperate to define temperature determining circuitry adapted to convert temperature readings from the thermistor to a useful form for regulating a source of heat, namely one or more of the heaters of the humidification system.

Typical components of the detection circuitry include an operational amplifier to amplify analog temperature readings from the thermistor, and an A/D converter to convert the amplified signals to the digital temperature signals or words. The temperature signal may be coupled to the + input of the amplifier. The operational parameters of the amplifier are typically set by resistors so as to have an offset and a gain determined by the impedance of the resistors. For example, a feedback resistor(s) interposed between the − input and the output of the amplifier and one or more of a tie-up (to the positive power supply rail) and/or tie-down (to the ground or negative power supply rail) resistor coupled to the − input of the amplifier sets the gain and offset of the amplifier. Ideally, the resistors are selected to set the amplifier to produce an output that can extend over the full extent of voltage in a generally linear range (or at least over a range that avoids an undesirably non-linear operating region) for the expected range of voltage at the + input.

By way of example, the resistance of a thermistor expected to encounter a range of temperatures between a low temperature and a high temperature will vary from an expected high impedance to an expected low impedance, respectively. The offset and gain of the amplifier are typically set such that the amplifier will output signals from about 0 volts to about 2.5 volts (by way of example) across the expected temperature range. The gain and offset may be provided by fixed resistances, or one or both may be manually adjusted such as where a selected resistance is provided by the setting of a potentiometer or the like. However, the components of the detection circuitry, such as the amplifier and associated resistors if not also the A/D converter, can drift over time such that the digital temperature signal may become inaccurate, or various of those components could fail altogether. Erroneous or otherwise useless data may thus result, leading to inaccurate or improper operation of the heater unit. As a result, it is customary to periodically take the heater units out of service for re-calibration by a technician, for example.

Conventional re-calibration may involve taking the heater unit to a workshop or other location, where it can be hooked up to test equipment to test operation of the detection circuitry. If the components have drifted, the technician may be able to at least partially restore the desired operating conditions such as by replacing some of the components or adjusting those that can be varied in situ, such as one or more potentiometers or the like. The re-calibrated heater unit is then returned to service. Conventional re-calibration of the heater unit presents a number of disadvantages. Often, the range over which adjustments can be made, such as of the potentiometers, is insufficient to restore the original operating range. Further, re-calibration may not always result in obtaining proper settings. Moreover, the heater unit may be operating for some period of time while not properly calibrated. Additionally, heater units may be taken out of service on a regular re-calibration schedule, even if it turns out that, on testing, the unit is still within specification. Thus, conventional re-calibration adds to cost and resource demands to users, not to mention the risk of delay in providing desired operation of a respiratory system.

SUMMARY OF THE INVENTION

The present invention provides a method and apparatus to automatically calibrate relative to the detection circuitry without the drawbacks associated with conventional re-calibration of heater units. To that end, and in accordance with the principals of the present invention, the detection circuitry is adapted to selectively couple to the thermistor or to at least a first source having an impedance corresponding to a temperature at which the amplifier would be expected to output a minimum voltage signal, and the processor is adapted to determine and output an adjustable offset signal which sets the offset of the amplifier based on digital temperature signals obtained from the first source. Typical of thermistors is that their impedance goes down as the temperature to which they are exposed goes up. In that case, the amplifier is expected to output a minimum voltage signal in response to an impedance representing the high end of the range of temperatures over which the thermistor is expect to be exposed. The first source may thus be selected to have an impedance corresponding to the expected impedance of the thermistor when exposed to a temperature at the high end of the expected temperature range.

In one embodiment, the offset signal from the processor is a digital word that is converted to an analog signal by a D/A converter, the output of which is coupled, such as via a resistor, to the amplifier input to thus provide automatic calibration of the offset by the processor, rather than requiring a technician to adjust same. Additionally, in one embodiment, while the processor is obtaining digital temperature signals from the first source, the processor adaptively adjusts the offset signal until the digital temperature signal from the detection circuitry sufficiently correlates to an expected digital signal. The offset signal thus obtained is then set for use as the offset of the amplifier during subsequent temperature readings from the thermistor.

The offset signal may be determined anew during a calibration process by an iterative comparison of the digital temperature signals (or useful values) from the first source to an expected digital temperature signal (or useful value). To that end, operational boundaries are used to set the offset signal in relation thereto, such as the average between upper and lower boundaries of operation, which may initially be set at the extreme limits of the processor word size. Until the difference between the boundaries is within a preset limit, such as less than one, the offset signal will be adjusted. The offset of the amplifier is thus adjusted to correspond to the average of the boundary parameters, and the digital temperature signal obtained while the detection circuitry is coupled to the first source is compared to a stored digital word expected to be obtained if the detection circuitry is proper calibrated. If the digital temperature signal is higher than the stored digital word, the lower boundary parameter is reset to the current value for the offset signal, and the process repeated. If the digital temperature signal is equal to or less than the stored digital word, the upper boundary parameter is reset to the current value for the offset signal, and the process repeated. The foregoing is repeated to iteratively set the offset signal until the difference between the boundary parameters is within range, whereat the offset signal producing that correlation is maintained as the offset signal until the next time the calibration process is run.

Advantageously, the amplifier is configured to have a gain which produces an output signal just below its useful maximum, such as a few millivolts below the normal linear range maximum. For example, if the maximum normal output is 2.5 volts, the gain is set so that in response to an input impedance which would otherwise produce a 2.5 volt output, the actual output would normally be slightly lower, such as about 2.445 volts, so that taking into account normal tolerance of the gain resistor(s) to be used, the output will not normally go into a region that is undesirably non-linear. With the gain thus established, a further feature of the present invention is to generate a scale factor used by the processor to take into account that the output range of the amplifier is deliberately set to avoid reaching the maximum voltage. To that end, and in accordance with the principles of the present invention, the detection circuitry is adapted to further selectively couple to a second source having an impedance corresponding to a temperature at which the amplifier would be expected to output the maximum voltage signal, and the processor is further adapted to determine a scale factor based on a relationship between the digital temperature signal obtained from the second source and the desired maximum output. Advantageously, the scale factor is determined by dividing the value for the desired maximum output and the signal obtained. The second source may be selected to have an impedance corresponding to the expected impedance of the thermistor when exposed to a temperature at the low end of the expected temperature range. If the maximum would desirably have been 2.5 volts, but due to the offset and behavior of the resistors involved, the output is somewhat less, say 2.448 volts, the scale factor would be 1.021. The processor will use that scale factor to adjust the digital temperature signal in order to obtain the useful value, such as by a computation or reference to a look-up table. In one embodiment, the digital temperature signal is multiplied by the scale factor, and the resulting word used to locate from a look-up table the temperature value which corresponds thereto, to thus provide a useful value representing the actual temperature at the probe.

The first and second sources may be fixed resistance, precision resistors, having respective resistance values corresponding to the expected impedance of the thermistor at or near the end points of the temperature range over which the thermistor is expected to be exposed. By utilizing two sources corresponding, for example, to the low and high ends of the expected temperature range, respectively, adjusting the offset and determining a scale factor results in adjusting the behavior of the temperature determining circuitry to respond in a manner correlated to the expected slope of the response of the thermistor resistance in relation to temperature, thus calibrating the heater unit to generate a useful form of signal reflective of the actual temperature to which the thermistor is exposed during normal operation of the heater unit.

The temperature determining circuitry can automatically switch between normal operation to a calibration mode. By way of example, on power-up of the heater unit, or whenever it comes out of standby mode, a calibration process is undertaken by which preset temperature readings are obtained from the first and/or second source(s) and calibration undertaken to automatically adjust the offset or scale factor as necessary. Advantageously, the offset is adjusted first, followed by determination of the scale factor. Thereafter, normal operation is restored and the detection circuitry coupled to the thermistor to obtain readings from the thermistor with the heater unit as calibrated. The foregoing avoids the need to take the heater unit out of service or to a workshop or other location, and also eliminates the need for a technician to hook the heater unit to test equipment, in order to undertake routine re-calibration. Moreover, the adjustability of the offset along with the ability to determine a scale factor provides a greater range of adjustment such that the desired operating conditions of the detection circuitry can be more reliably or more closely restored. Particularly advantageously, the scale factor is utilized by the processor so as not to require actual adjustment of the amplifier gain which would otherwise present limits in order to avoid operating the amplifier in an undesirably non-linear range. Additionally, the heater unit adapted with the features of the present invention is not likely to be operating for any significant period of time while not properly calibrated, yet there is no need to take the heater unit out of service only to find that it is operating within specification.

In accordance with a further aspect of the present invention, if the detection circuitry has failed or drifted beyond acceptable limits, attempts to adjust the offset signal will result in an offset signal that is outside of an acceptable range and/or the scale factor will exceed a permissible range. In either situation, the heater unit will be considered to have failed and not able to be automatically calibrated or to function reliably. Rather, a failure will be determined and indicated such as by issuing an alarm and/or disabling power to the heater(s) so as to shut down the heater unit. As a consequence, the heater unit may be kept in operation while it is operating properly, and removed from service only when repair is needed.

By virtue of the foregoing there is thus provided a method and apparatus to automatically calibrate relative to the detection circuitry without the drawbacks associated with conventional re-calibration of heater units. These and other objects and advantages of the present invention shall be made apparent from the accompanying drawings and the description thereof.

BRIEF DESCRIPTION OF THE DRAWINGS

The accompanying drawings, which are incorporated in and constitute a part of this specification, illustrate an embodiment of the invention and, together with the general description of the invention given above and the detailed description of the embodiment given below, serve to explain the principles of the present invention.

DETAILED DESCRIPTION OF THE DRAWINGS

Figure 1:
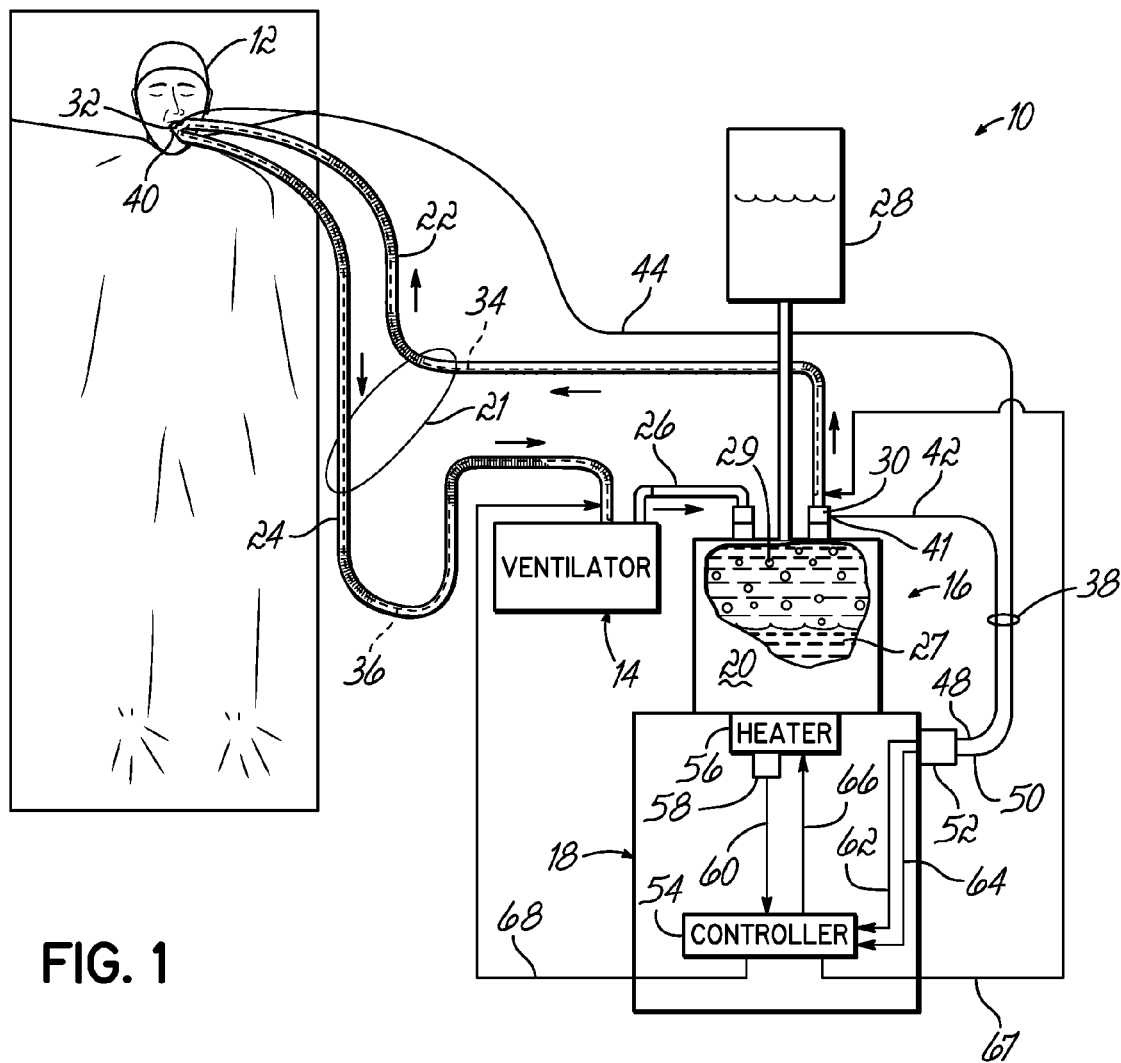
FIG. 1 is a diagram of a respiratory system having a heater unit adapted with features constructed in accordance with the principles of the present the present invention.

FIG. 1 shows an exemplary respiratory system 10 for supplying breathable gases to a patient 12. In the illustrated embodiment, the respiratory system 10 includes a ventilator 14, a humidification system 16 having a heater unit 18, a heatable container for water such as a disposable chamber 20, and a breathing circuit 21 having a first elongated hose or conduit 22 defining an inspiratory limb 22 and a second elongated hose or conduit 24 defining an expiratory limb 24.

Ventilator 14 drives breathable gas, such as oxygen, anesthetic gas and/or air, through gas conduit 26 and into an air inlet of chamber 20. Water 27 is received in chamber 20, either by being poured in manually or automatically from a water supply 28 such as a bag or bottle, and which may be vented. Chamber 20 is heated by heater unit 18 to heat up the water 27 therein. Heated water vapor 29 may also be produced within chamber 20 above the level of water 27 therein. The gas from conduit 26 passes over or through the heated water 27 and/or through heated water vapor 29 to become heated and humidified before exiting the chamber 20 as heated and humidified gas.

The heated and humidified gas flows from chamber 20 to the patient 12 by passing through inspiratory limb 22. A first end of inspiratory limb 22 is coupled to chamber 20 by a connecting member or joint 30, and a second end of inspiratory limb 22 is coupled to a breathing attachment 32 that facilitates delivery of the gas passed there through to the patient 12. The breathing attachment 32 may couple to an invasive apparatus such as an endotracheal tube, or a non-invasive apparatus such as a mask (both not shown) that promotes gas delivery. The gas may be further heated while passing through inspiratory limb 22 to breathing attachment 32 by heater circuit 34 associated with inspiratory limb 22. Expiratory limb 24 allows exhaled air and other gas expelled from patient 12 to pass back to ventilator 14. Another heater circuit 36 is associated with expiratory limb 24 for heating the expelled gas. Heater circuits 34 and 36 may be comprised of one or more elongated, coiled heater wires extending along or through limbs 22 and 24, respectively, although different types of heater circuits or wire configurations could be employed.

Respiratory system 10 may also include a patient temperature cable (PTC) 38 having one or more temperature responsive devices such as thermistors 40, 41 (which may be encased in probes, not shown) to provide thermal feedback in the form of temperature readings to heater unit 18 for purposes to be described. Temperature cable 38 includes a first communication cable 42 and a second communication cable 44. Thermistor 41 is coupled to joint 30 at the entry to inspiratory limb 22 to provide a temperature reading via first communication cable 42 indicative of the actual measured temperature of the heated and humidified gas exiting from chamber 20 ("the output temperature"). Thermistor 40 is coupled to breathing attachment 32 at the exit of inspiratory limb 22 to provide a temperature reading via second communication cable 44 indicative of the actual measured temperature of the humidified gas being provided to the patient ("the patient temperature"). First communication cable 42 has an end 48 coupled to heater unit 18 to communicate the output temperature to heater unit 18. Similarly, second communication cable 44 has an end 50 coupled to heater unit 18 to communicate the patient temperature to heater unit 18. Ends 48 and 50 may be advantageously secured together through a connector 52 to facilitate coupling the first and second cables 42, 44 to a mating socket (not shown) on heater unit 18. Further details of a suitable cable 38 and probes for thermistors 40 or 41 are set out in concurrently-filed U.S. patent application Ser. No. 11/927,020, and concurrently-filed U.S. patent application Ser. No. 11/927,077, the disclosures of both of which are incorporated herein in their entirety by reference.

Heater unit 18 includes a controller 54 and a heater 56 in the form of a hot plate heater. An example of one suitable heater 56 is described in concurrently-filed U.S. patent application Ser. No. 11/926,982 the disclosure of which is incorporated herein by reference in its entirety. Thermally coupled to heater 56 is a temperature responsive device such as a thermistor 58 to provide readings of the actual measured temperature of heater 56 to controller 54 ("the input temperature"). The input temperature is representative of the heat input to the chamber 20, and is coupled to controller 54 as at 60. The output temperature readings and the patient temperature readings are also coupled to controller 54 as at 62, 64, respectively. The various temperature readings are utilized by controller 54 to control the functions of heater unit 18 including regulating the temperature of heater 56 and heater circuits 34 and 36 such as with power signals 66 for heater 56 and power signals 67, 68 for heater circuits 34, 36, respectively. Examples thereof are shown in concurrently-filed U.S. patent application Ser. No. 11/926,990; U.S. patent application Ser. No. 11/927,013; U.S. patent application Ser. No. 11/927,054; and/or U.S. patent application Ser. No. 11/927,068; the disclosures of all four of which are incorporated herein by reference in their respective entirety. Controller 54 may also be adapted to detect presence of a heated breathing circuit 21 as described in concurrently-filed U.S. patent application Ser. No. 11/927,004 the disclosure of which is also incorporated herein by reference in its entirety.

Figure 2:
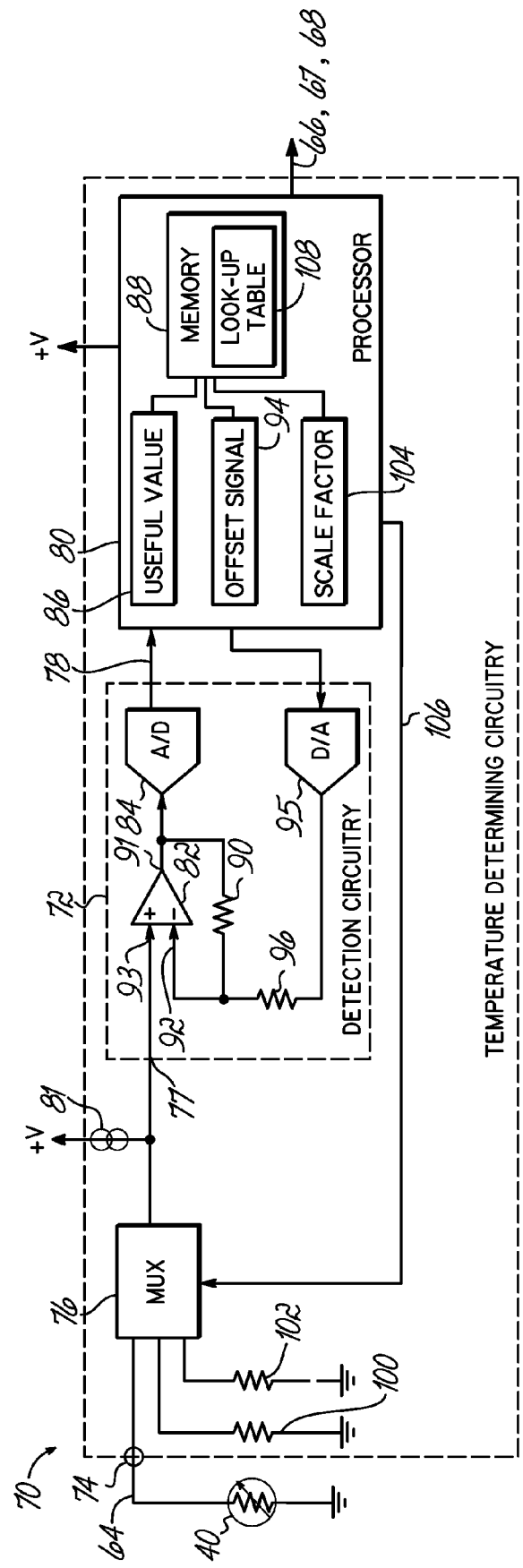
FIG. 2 is a schematic diagram of an example of automatically calibrating temperature determining circuitry in accordance with the principles of the present invention and implemented in the heater unit of FIG. 1.

In order to properly utilize the temperature readings from respective thermistors 40, 41, and 58, each may be selectively coupled to a respective automatically self-calibrating thermistor circuit 70, in the form of temperature determining circuitry, as will be described with further reference to FIG. 2 in relation to thermistor 40, it being understood that the circuitry and its operation may be used instead for thermistor 41 or may be replicated therefor, and may also be used or replicated for thermistor 58. Circuitry 70 includes detection circuitry 72 and is constructed in accordance with the principles of the present invention to provide automatic calibration to avoid or reduce problems which might otherwise develop over time, such as due to drift of the components of detection circuitry 72, and which might otherwise require taking heater unit 18 out of service for a technician to attempt to calibrate. To that end, circuitry 70, which may form or be part of controller 54, includes a port 74, which may be a connector or plug socket for PTC cable 38, adapted to be coupled such as at 64 to thermistor 40. Port 74 is coupled to a multiplexer ("MUX") 76 of circuitry 70, which in turn is coupled to the input 77 of detection circuitry 72 so as to selectively couple temperature readings from thermistor 40 coupled to port 74 to detection circuitry 72.

Temperature readings may be of the impedance of thermistor 40, but typically would be in the form of a voltage across thermistor 40 as induced by a constant current therethrough as at 81. Detection circuitry 72 includes output 78 which is coupled to processor 80. Temperature readings are coupled through amplifier 82 and A/D converter 84 of detection circuitry 72 to provide digital temperature signals at output 78 representative of the temperature readings at input 77. Processor 80 is adapted to generate from digital temperature signals at 78 a useful value signal 86 correlated to the temperature at thermistor 40 based on values and programs stored in one or more memory components 88 communicating with, or forming part of, processor 80 (memory 88 is shown as internal of processor 80 but as will be readily appreciated could, in whole or in part, be external thereof).

Amplifier 82 is an operational amplifier with feedback resistor(s) 90 coupled between its output 91 and its − input 92 and an offset voltage coupled via resistor 96 to − input 92 for purposes of setting the gain of amplifier 82, and the offset as will be described. Temperature readings from thermistor 40 are coupled to the + input 93 of amplifier 82. Amplifier 82 has a normal operating range over which the voltage at output 91 will vary between minimum and maximum values, with the range advantageously not including any portion which is undesirably non-linear. The range may more advantageously be substantially linear. By way of example, the range may be expected to extend between 0 volts and 2.5 volts. In that example, the maximum impedance (i.e., the maximum voltage across thermistor 40) expected to be seen at input 77 of detection circuitry 72 (which corresponds to the low end of the expected temperature range to which thermistor 40 is expected to be exposed) should result in a maximum value of the voltage at output 91 of no more than about 2.5 volts. The impedance of feedback resistor(s) 90 and/or offset resistor 96 may thus be selected such that the maximum output under such circumstances is 2.5 volts. More advantageously, however, the impedance of resistors 90, 96 may be selected such that the voltage at output 91 is slightly less than that maximum value taking into account the tolerance of the components of detection circuitry 72, such as amplifier 82, resistors 90, 96 and A/D converter 84. The output at 91 maximum may thus be limited so that the voltage will not reach the maximum, but will instead reach a few millivolts below that maximum for purposes to be explained hereinafter.

Amplifier 82 also is provided with an offset at its − input 92. More particularly, processor 80 is adapted to generate an offset signal 94, in the form of a digital word, which is coupled via D/A converter 95 through resistor 96 to amplifier − input 92. Advantageously, the offset signal 94 is a variable which is determined, as will be described, to ensure that the minimum voltage output by amplifier 82 at output 91 is zero volts, or a few millivolts above zero in response to the minimum impedance (i.e., the minimum voltage across thermistor 40) expected to be seen at input 77 of detection circuitry 72 corresponding to the high end of the expected temperature range to which thermistor 40 is expected to be exposed.

Temperature determining circuitry 70 is provided with at least a first source 100, such as a precision resistor, having an impedance corresponding to the impedance expected from thermistor 40 when exposed to a patient temperature at a heated location such breathing attachment 32 at the high end of the expected temperature range thereof. For thermistor 40, the high end may be 45° C. with first source 100 having an impedance of 4.248 Kohms (for thermistor 41 exposed to an output temperature at a heated location such as joint 30, the high end may be 75° C., with first source 100 having an impedance of 1.48 Kohms). Input 77 of detection circuitry may be selectively coupled to first source 100 via MUX 76 such that the temperature reading from first source 100 causes amplifier 82 to output a voltage at output 91 which is intended to be a minimum voltage. That output is converted to a digital temperature signal at 78. Processor 80 determines an offset signal 94 to thus set the variable offset at input 92 of amplifier 82 based on the digital temperature signal 78 from first source 100 to achieve substantially the desired minimum voltage at output 91 thereby providing automatic calibration.

In the embodiment shown herein, temperature determining circuitry 70 is also provided with a second source 102, such as a precision resistor, having an impedance corresponding to the impedance expected from thermistor 40 when exposed to a temperature at breathing attachment 32 56 at the low end of the expected temperature range thereof, which may be 10° C. and second source 102 having an impedance of 17.58 Kohms (for thermistor 41, the low end may be 20° C. and first source 102 may have an impedance of 12.499 Kohms). Input 77 of detection circuitry may be selectively coupled to second source 102 via MUX 76 such that the temperature reading from second source 102 results in a maximum voltage at output 91 and is converted to a digital temperature signal at

78. Processor 80 determines a scale factor 104 based on the digital temperature signal 78 from second source 102 in relation to a desired maximum output voltage of amplifier 82 so as to automatically calibrate for the gain of amplifier 82. If the maximum would desirably have been 2.5 volts, but due to the offset and behavior of the resistors involved, the output is somewhat less, say 2.448 volts, the scale factor is determined by dividing the desired by the actual (i.e., 2.5/2.448) to, in this instance, obtain a scale factor of 1.021. The processor will use that scale factor to adjust the digital temperature signal obtained from thermistor 40 in order to obtain the useful value 86, such as by a computation or reference to a look-up table.

Figure 3:
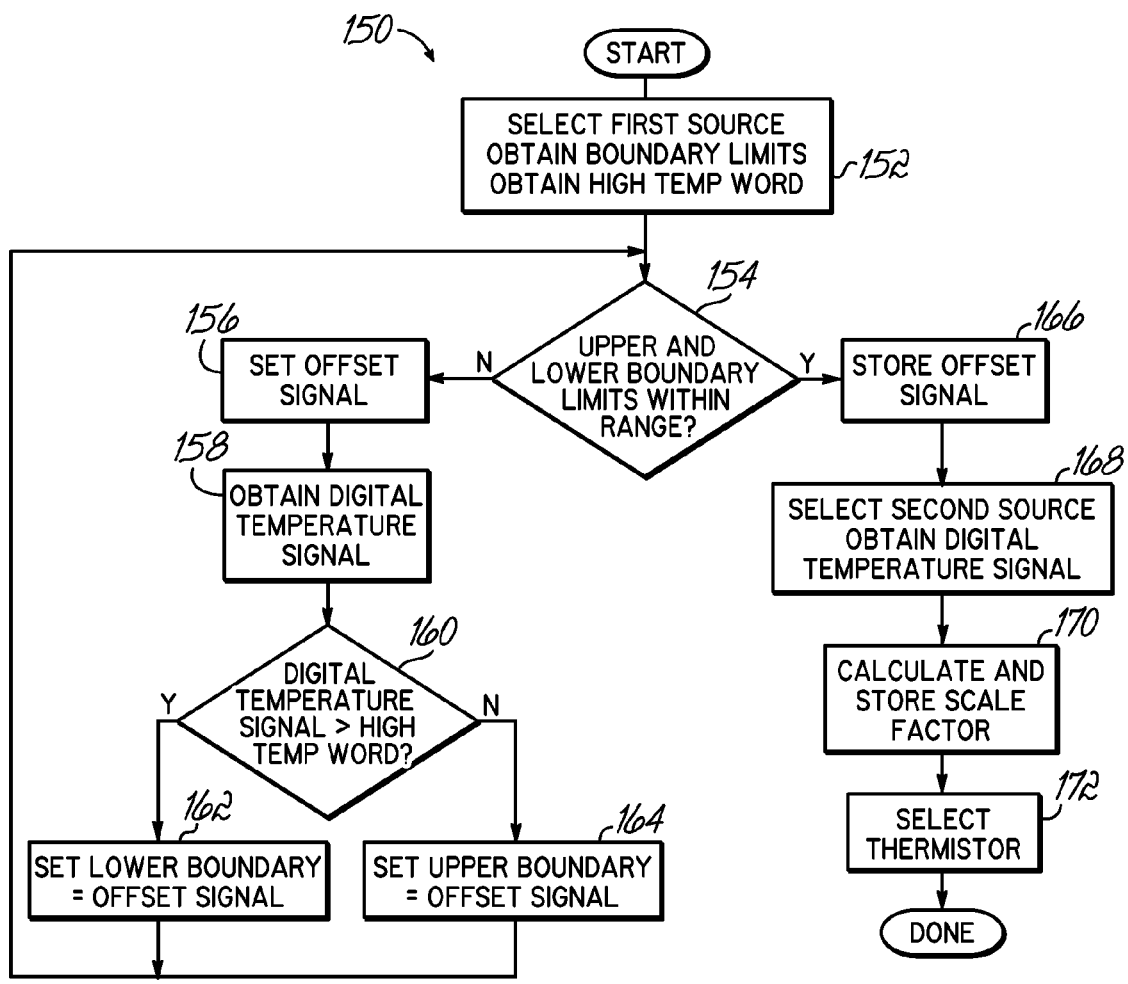
FIG. 3 is a flowchart demonstrating the steps executable by the automatically calibrating temperature determining circuitry of FIG. 2.

Processor 80 outputs a selector signal at 106 by which to set MUX 76 to selectively couple port 74 or at least first source 100 to detection circuitry 72. Selector signal 106 may further set MUX 76 to instead selectively couple second source 102 to detection circuitry 72. During normal or humidifying operation of heater unit 18, processor 80 will output selector signal 106 to selectively couple port 74, and thus thermistor 40, to detection circuitry 72 in order for processor 80 to obtain temperature readings therefrom in the form of digital temperature signals which processor 80 can then use to generate the useful values 86 corresponding to the patient temperature to which thermistor 40 is exposed. A similar circuit(s) 70, sharing processor 80 and with appropriately selected first and second sources 100, 102, may be provided for thermistor 41 with respect to output temperatures to which it is exposed at joint 30 and/or for thermistor 56 with respect to input temperatures to which it is exposed to a heated location at heater 56. Processor 80 can initiate a calibration mode, such as during power-up or restart after a standby of heater unit 18, in order to automatically calibrate for potential drift or the like of detection circuitry 72. To that end, processor 80 is adapted to run a calibration process 150 as will now be described and with reference to FIG. 3.

At step 152, processor 80 outputs selector signal 106 to cause MUX 76 to couple first source 100 to the input 77 of detection circuitry 72 such that the temperature reading from first source 100 is converted to a digital temperature signal 78. Digital temperature signal 78 should correspond to a low digital word value as would correspond to a high temperature. For that purpose, a high temp digital word is stored in memory 88 during manufacture of heater unit 18 corresponding to a digital temperature signal 78 reflecting the minimum desired output voltage output of amplifier 82 when the associated thermistor 40, 41 or 58 is exposed to a temperature at the high end of the expected range of temperatures of the associated heated space (such as breathing attachment 32, joint 30, or heater plate 56, respectively). That minimum voltage may be zero or is advantageously set to be a few millivolts above zero so as to avoid operation of amplifier in an undesirably non-linear range. Where a 12 bit word set is used by processor 80, the high temp digital word will typically be a value between 0 and 4095, and likely closer to zero, but may advantageously be slightly more than zero (such as 16, digitally) so as to produce an offset for amplifier 82 such that at a minimum impedance input, the output is a few millivolts above zero.

Also at step 152, a set of lower and upper boundaries limits (such as 0 and 4095, respectively, corresponding to the limits of a 12 bit digital word length as might be used by processor 80) are recalled from memory 88 and set as lower and upper boundary values. At step 154, the lower and upper boundary values are compared. If they are not within an expected range (such as where the difference therebetween is less than one), then the offset signal 94 is not yet properly set and the process branches step 156 whereat the offset signal 94 is set to correspond (such as equal to) an average of the upper and lower boundary values. The offset signal 94 adjusts behavior of amplifier 82 and, after a brief settling period (such as to allow transients time to decay), a digital temperature signal 78 from first source 100 is obtained at step 158. At step 160, the digital temperature signal obtained at step 158 is compared to the high temp digital word. If, at step 160 the digital temperature signal is greater than the high temp digital word, the process goes to step 162 whereat the lower boundary value is reset to the current value for the offset signal and the process returns to step 154 to be repeated. If, however, at step 160, the digital temperature signal is equal to or less than the high temp digital word, the process goes to step 164 whereat the upper boundary value is reset to the current value for the offset signal and the process returns to step 154 to be repeated. The process is repeated to iteratively adjust offset signal 94 until the digital temperature signal 78 obtained from first source 100 correlates to an expected value represented by the high temp digital word. Once the correlation is satisfied, which in the embodiment described herein is determined by comparing the lower and upper boundary values for satisfaction of a predetermined relationship (such as a difference therebetween of less than one) at step 154, the offset signal 94 obtained in the last pass through step 156 is retained at step 166 to be used for the offset of amplifier 82 for subsequent, normal humidifying operation of heater unit 18 until the next time process 150 is undertaken.

After the offset signal 94 has thus been determined, in some embodiments, automatic calibration may be considered completed. In the embodiment described herein, before the automatic calibration is considered complete, processor 80 also determines a scale factor 104 as will now be described. To that end, the process continues to step 168 whereat processor 80 outputs a selector signal 106 to cause MUX 76 to couple second source 102 to the input 77 of detection circuitry 72 such that, after a settling period, a temperature reading is obtained from second source 102 and converted to a digital temperature signal 78. As amplifier 82 was set to have a gain that would cause its maximum output voltage to be slightly below the normally desired maximum, such as by a few millivolts, the digital temperature signal obtained from second source 102 will be slightly less than the normally desired maximum. To effectively adjust the gain of amplifier 82 without actually changing its gain, scale factor 104 is computed at step 170 as the positive result of the division of the digital temperature signal into a digital word corresponding to what would have been expected as the digital temperature word 78 had amplifier 82 had its gain set to output the maximum value. In the embodiment shown herein, the maximum output value is 2.5 volts, but the gain of amplifier 82 is set such that the actual maximum is typically a few millivolts less, such as 2.448 volts nominal, in which event the scale factor 104 is accordingly a digital word corresponding to the result of the division of 2.448 into 2.5, namely, 1.021. The digital temperature signal may be adjusted, such as by subtracting a digital value of 16 therefrom to account for the minimum offset described earlier, before being used in the computation of the scale factor 104.

After having determined the offset signal 94 and the scale factor 104, calibration can be considered completed in the embodiment shown herein. Note that a process 150 may be separately undertaken for each of thermistors 40, 41 and/or 58 in order to set the gain and scale factor for each of circuitry 70 associated therewith. When calibration is considered complete, the process goes to step 172 whereat processor 80 outputs select signal 106 to cause MUX 76 to couple port 74, and thus a thermistor 40 (or 41 or 58) if coupled thereto, to the input 77 of detection circuitry 72 and process 150 ends.

Processor 80 thereafter operates heater unit 18 in a normal, humidifying mode with temperature readings from respective thermistors 40, 41 and/or 58 each being converted to digital temperature signals 78 for use by processor 80 in generating useful values 86. In that regard, processor 80 includes in memory 88 a look-up table 108 which converts the digital temperature signal, as scaled, to a useful value which is representative of the actual temperature as sensed by the respective thermistor 40, 41 or 58. To that end, a digital temperature signal from A/D converter 84 is multiplied in relation to the scale factor 104 such as by multiplying the digital temperature signal (which may first be reduced by digital 16 as above-described) by the scaling factor 104 to produce an index or address look-up signal used by processor 80 to retrieves a useful value 86 from look-up table 108. The useful value 86 for each of the thermistors 40, 41 and/or 58 are used by processor 80 to control the operations of heater unit 18, and particularly to regulate the temperature of, and/or to disable, heaters 34, 36 and/or 56 by power signals 67, 68 and 66, respectively as explained by way of example in aforementioned concurrently-filed U.S. patent application Ser. No. 11/926,990; U.S. patent application Ser. No. 11/927,013; U.S. patent application Ser. No. 11/927,054; and/or U.S. patent application Ser. No. 11/927,068.

The values for look-up table 108 are programmed therein based on computations made in relation to the expected behavior of the thermistor 40, 41, or 58. A specimen thermistor can be exposed to various temperatures, and the digital temperature signals, as scaled, obtained therefrom to generate the values in the look-up table. Advantageously, however, the thermistor characteristics are known and a formula can be applied to determine a correlation between the impedance and the expected useful value, taking into account the detection circuit 72 in terms of its known components (based on nominal values thereof) and the desired minimum voltage for the offset and the nominal gain. By way of example, the gain resistor(s) 90 may be 32.6 Kohms, resistor 96 may be 26.7 Kohms, constant current from 81 may be 100 microamps, and the offset signal 94 and scale factor 104 may be ignored. A computer may utilizes a formula to relate those values to the expected range of impedance of the thermistor relative to a digital word range for the table array size to calculate a range of useful values over the impedance range of the thermistor with respect to the expected temperature range, and those values are programmed into look-up table 108.

One look-up table 108 may be used for all three thermistors, although each may advantageously have its own look-up table 108. Alternatively, or additionally, one or more of the thermistors may produce a useful value by implementing the above-mentioned formula within processor 80, rather than in advance to generate the look-up table values. Use of a look-up table(s) is advantageous, however, as it reduces the computational load on processor 80 during use of heater unit 18. Also, thermistor 58 may not require the same precision as do thermistors 40 and/or 41, as heater unit 18 advantageously controls the temperature of heater 56 and/or breathing circuits 34, 36 in relation to the temperatures from one or more of probes 40, 41, with the temperature of hot plate heater 56 being monitored primarily for safety purposes, such as to cause processor 80 to disable the heater(s) and/or generate alarms if heater 56 gets too hot. Thus, thermistor 58 may not require a calibrated circuit, and may simply couple via a pre-set amplifier and A/D converter to processor 80 to obtain useful values that are not as precise but are sufficient for monitoring heater 56 within certain desirable safety limits.

During calibration process 150, if components of detection circuitry 72 have drifted out of an acceptable range or parts have failed (whether in detection circuitry 72 or between processor 80 and port 74 such as due to an open or failed line or circuit component), attempts to adjust offset signal 94 will result in an offset signal that is outside of an acceptable range and/or the scale factor 104 will be outside a permissible range. Processor 80 is adapted to determine a failure should either or both occur. To that end, before proceeding to step 168, a test may be undertaken of the offset signal 94. In one embodiment, the offset of amplifier 82 should be something greater than zero, and may typically be about 0.8826 to 0.9683 volts. Hence, if the offset signal 94 is ultimately determined to be a value that would cause the output of D/A converter 95 to produce an offset outside of that range, then a failure is determined by processor 80 and is indicated by issuing a visual and/or audible alarm to alert a user (not shown) that the heater unit 18 has failed so that it can be serviced and/or generating or interrupting the power signal(s) to the heater(s) to thus disable the heater(s).

If the offset signal 94 is within the acceptable range, before completing calibration, the scale factor is also tested, such as in step 178, to see that it, too, does not exceed a permissible range. In one embodiment, the gain of amplifier 82 is nominally set to provide a maximum voltage at output 91 in response to a maximum expected impedance (such as represented by second source 102) of 2.445 volts, such that the scale factor might typically be expected to be equivalent to 0.055 volts (in digital terms, 1.022). Due to variations in components, such as within tolerance limits, and due to drift over time, the actual maximum may vary between 2.374 and 2.499 volts, such that the scale factor may vary between 0.1.0005 (equivalent to about 0.0001 volts) and 0.1.053 (equivalent to about 0.13 volts). If, however, the scale factor 104 at step 178 is greater than 1.053, then the digital temperature signal 78 from second source 102 cannot provide a high enough output and a failure is determined with the indication(s) as described above. Similarly, if the scale factor goes below 1.0005, then there is the possibility that amplifier 82 will begin to enter into an undesirably non-linear operating region and a failure is determined, again with the indication(s) described above. Processor 80 may store in memory 88 indicators or flags to indicate to a technician the nature of the failure to facilitate troubleshooting of heater unit 18. Offset signal 94 need not be tested before determining the scale factor 104. Instead, both offset signal 94 and scale factor 106 may be tested after calculation of scale factor 104.

Also, during normal operation, if the connection to the thermistor fails, such as due to an open or short in PTC 38, digital temperature signal 78 from the thermistor will result in a look-up table index or address that is out of the range thereof. In that circumstance, a failure will also be determined and an appropriate alarm given and/or the heater(s) disabled.

In use, heater unit 18 will periodically enter into the calibration process 150 to determine the offset for amplifier 82 and a scale factor 104. Heater unit 18 will then operate normally for humidification purposes by obtaining temperature readings as desired or needed from the appropriate thermistor 40, 41 and/or 58 by which to control operation of heater unit 18 such as to regulate the temperature of heaters 34, 36 and/or 56. If, during the calibration process of circuitry 70 for a respective thermistor, a failure in the offset signal 94 or scale factor 106 is determined, heater unit 18 will generate an alarm and/or disable the heater(s). Also, during normal, humidifying operation, if a look-up attempt exceeds the range of the look-up table 108, a failure will be determined. By virtue of the foregoing, there is thus provided a method and apparatus to automatically calibrate relative to the detection circuitry without the drawbacks associated with conventional re-calibration of heater units.

While the invention has been illustrated by the description of an embodiment thereof, and while the embodiment has been described in considerable detail, it is not intended to restrict or in any way limit the scope of the appended claims to such detail. Additional advantages and modifications will readily appear to those skilled in the art. By way of example, a further source representing a temperature between the ends of the expected temperature range may be included and the calibration process expanded to account therefore so as to better fit or model the behavior of the thermistor(s). Moreover, while the invention is described in the context of a ventilator based humidification system 16, it will be appreciated that the principles of the invention are applicable to thermistor circuitry generally and to a heater system in which a heater is to be monitored thereby. To that end, humidification system could be driven by a hospital oxygen supply, or be part of a CPAP or BiPAP system, rather than form part of a ventilator-based system. The invention in its broader aspects is therefore not limited to the specific details, representative apparatus and methods and illustrative examples shown and described. Accordingly, departures may be made from such details without departing from the scope or spirit of Applicants' general inventive concept.

Having described the invention, what is claimed is:

1. An automatically calibrating thermistor circuit comprising:
   a port coupleable to a thermistor exposed to a heated location over which a range of temperatures is expected, and configured to obtain a temperature reading representative of a temperature of said heated location;
   a first source, the first source providing a temperature reading associated with one end of said expected range of temperatures; and
   detection circuitry having an input selectively coupleable to the port and the first source and having an output, the detection circuitry including an amplifier coupled to the input and having a generally preset gain and a variable offset, the variable offset being set in response to an adjustable offset signal coupled thereto, and an A/D converter coupled to the amplifier and the output by which to provide a digital temperature signal correlated to a temperature reading at the input, the amplifier outputting amplified temperature reading signals across an expected operating range in relation to said expected temperature range of said heated location, the amplifier outputting a minimum value in response to the first source; and
   a processor coupled to the detection circuitry output, the processor selectively causing the first source to be coupled to the input of the detection circuitry in a calibration mode and the port to be coupled to the input of the detection circuitry in a normal operation mode, in the calibration mode the processor determining the adjustable offset signal based on the digital temperature signals obtained from the first source, the adjustable offset signal being operatively coupled to the variable offset of the amplifier such that the variable offset of the amplifier is set in response to the adjustable offset signal from the processor so that the variable offset of the amplifier is based on digital temperature signals obtained from the first source whereby to obtain the temperature reading representative of said temperature of said heated location in the normal operation mode.

2. The automatically calibrating thermistor circuit of claim 1, the first source being a precision resistor having an impedance associated with a high end of said expected temperature range.

3. The automatically calibrating thermistor circuit of claim 1 further comprising a multiplexer responsive to the processor to selectively couple the port or the first source to the detection circuitry.

4. The automatically calibrating thermistor circuit of claim 1 further comprising a D/A converter coupling the offset signal from the processor to the amplifier.

5. The automatically calibrating thermistor circuit of claim 1, the processor further iteratively adjusting the offset signal until the digital temperature signal from the detection circuitry correlates to an expected digital signal.

6. The automatically calibrating thermistor circuit of claim 5, the processor further iteratively outputting as an offset signal an average of upper and lower boundary values and varying the boundary values in relation to the digital temperature signal from the detection circuitry until the boundary values satisfy a predetermined criterion.

7. The automatically calibrating thermistor circuit of claim 1, the processor further indicating failure in response to determining an offset signal that is outside of an acceptable range.

8. The automatically calibrating thermistor circuit of claim 1 further comprising a second source providing a temperature reading related to a second temperature associated with another end of said expected range of temperatures to cause the amplifier to output a maximum value, the detection circuitry input further selectively coupleable to the second source, the processor further selectively causing one of the first source and the second source to be coupled to the input of the detection circuitry in the calibration mode, the processor determining a scale factor based on a relationship between the digital temperature signal obtained from the second source and a desired maximum output of the amplifier, the processor adjusting the digital temperature signals obtained from the port in relation to the scale factor in the normal operation mode.

9. The automatically calibrating thermistor circuit of claim 8, the second source being a precision resistor having an impedance associated with a low end of said expected temperature range.

10. The automatically calibrating thermistor circuit of claim 8 further comprising a multiplexer responsive to the processor to selectively couple the port, the first source, or the second source to the detection circuitry.

11. The automatically calibrating thermistor circuit of claim 8, the gain of the amplifier being preset to provide a maximum output of the amplifier below the upper end of the expected operating range of the amplifier.

12. The automatically calibrating thermistor circuit of claim 8, the processor indicating failure in response to determining the scale factor is outside a permissible range.

13. An automatically calibrating thermistor circuit comprising:
   a port coupleable to a thermistor exposed to a heated location over which a range of temperatures is expected, and configured to obtain a temperature reading representative of a temperature of said heated location;
   a first source, the first source providing a temperature reading associated with one end of said expected range of temperatures; and
   detection circuitry having an input selectively coupleable to the port and the first source and having an output, the detection circuitry including an amplifier coupled to the input and having a generally preset gain and a variable offset, the variable offset being set in response to an adjustable offset signal coupled thereto, and an A/D converter coupled to the amplifier and the output by which to provide a digital temperature signal correlated to a temperature reading at the input, the amplifier outputting amplified temperature reading signals across an expected operating range in relation to said expected temperature range of said heated location, the amplifier outputting a minimum value in response to the first source; and a processor coupled to the detection circuitry output, the processor selectively causing the first source to be coupled the input of the detection circuitry in a calibration mode and the port to be coupled to the input of the detection circuitry in a normal operation mode, in the calibration mode the processor determining the adjustable offset signal based on the digital temperature signals obtained from the first source, the processor further indicating failure if the adjustable offset signal determined by the processor is outside of an acceptable range.

14. The automatically calibrating thermistor circuit of claim 13 further comprising a second source providing a temperature reading related to a second temperature associated with another end of said expected range of temperatures to cause the amplifier to output a maximum value, the detection circuitry input further selectively coupleable to the second source, the processor further selectively causing one of the first source and the second source to be coupled to the input of the detection circuitry in the calibration mode, the processor determining a scale factor based on a relationship between the digital temperature signal obtained from the second source and a desired maximum output of the amplifier and indicating a failure in response to determining the scale factor exceeds a permissible value.

15. A method of automatically calibrating a thermistor circuit in which a thermistor is to be exposed to heat from a heated location, the temperature of which is expected to vary over a range of temperatures comprising:

operating a processor to selectively couple temperature readings from a first source providing a temperature reading associated with one end of said expected range of temperatures, through an amplifier having a generally preset gain and a variable offset, the variable offset being set in response to an adjustable offset signal coupled thereto, and an A/D converter to generate digital temperature signals corresponding to the temperature readings, the amplifier outputting amplified temperature reading signals across an expected operating range in relation to the expected temperature range, the temperature reading provided by the first source corresponding to a minimum value output of the amplifier;

determining with the processor the adjustable offset signal based on digital temperature signals obtained from the first source;

automatically setting the variable offset of the amplifier in response to the adjustable offset signal determined by the processor so that the variable offset of the amplifier is based on the digital temperature signals obtained from the first source;

thereafter, with the variable offset of the amplifier set in response to the adjustable offset signal determined by the processor, operating the processor to selectively couple temperature readings from the thermistor through the amplifier and the A/D converter to generate digital temperature signals corresponding the temperature readings from the thermistor; and determining with the processor a temperature of said heated location based on the digital temperature signals obtained from the thermistor.

16. The method of claim 15 further comprising determining the adjustable offset signal by iteratively adjusting the offset signal until the digital temperature signal obtained from the first source correlates to an expected digital signal.

17. The method of claim 16 further comprising iteratively determining the offset signal as an average of upper and lower boundary values and varying the boundary values in relation to the digital temperature signal from the A/D converter until the boundary values satisfy a predetermined criterion.

18. The method of claim 17 further comprising initially setting the boundary values to respective minimum and maximum values.

19. The method of claim 15 further comprising indicating failure if the offset signal determined is outside of an acceptable range.

20. The method of claim 15 further comprising:

coupling a temperature reading from a second source providing a temperature reading associated with another end of said expected range of temperatures through the amplifier and the A/D converter to generate a digital temperature signal corresponding to the temperature reading from the second source, the temperature reading provided by the second source corresponding to a maximum value output of the amplifier;

determining with the processor a scale factor based on a relationship between the digital temperature signal corresponding to the temperature reading from the second source and a desired maximum output of the amplifier; and adjusting the digital temperature signals corresponding to the temperature readings from the thermistor in relation to the scale factor.

21. The method of claim 20 further comprising setting gain of the amplifier to provide a maximum value output below the desired maximum output.

22. The method of claim 20 further comprising indicating failure if the scale factor is outside a permissible range.

* * * * *

UNITED STATES PATENT AND TRADEMARK OFFICE
CERTIFICATE OF CORRECTION

| | | |
|---|---|---|
| PATENT NO. | : 8,197,123 B2 | Page 1 of 1 |
| APPLICATION NO. | : 11/927000 | |
| DATED | : June 12, 2012 | |
| INVENTOR(S) | : Robert L. Snyder et al. | |

It is certified that error appears in the above-identified patent and that said Letters Patent is hereby corrected as shown below:

Title page, item (74) Attorney, Agent, or Firm, "Kurt L. Grossman" should be

-- Wood, Herron & Evans, LLP --

Column 3, line 15-16, "principals" should be -- principles --

Column 3, line 60, "proper calibrated" should be -- properly calibrated --

Column 5, line 49, "the present the present" should be -- the present --

Column 8, line 39, "such breathing" should be -- such as at breathing --

Column 8, line 59, "attachment 32 56" should be -- attachment 32 --

Column 9, line 45, "output voltage output of" should be -- voltage output from --

Column 11, line 12, "by digital 16" should be -- by the digital value of 16 --

Column 11, line 14, "retrieves" should be -- retrieve --

Column 11, line 40, "utilizes" should be -- utilize --

Claim 13, column 15, line 13, "coupled the input" should be -- coupled to the input --

Claim 15, column 16, line 11, "corresponding the temperature" should be -- corresponding to the temperature --

Signed and Sealed this
Fourteenth Day of August, 2012

David J. Kappos
*Director of the United States Patent and Trademark Office*